United States Patent [19]

Bowler et al.

[11] 4,115,580

[45] Sep. 19, 1978

[54] 3,4-EPOXY-CYCLOPENTA-1,2-DIYL PROSTANES

[75] Inventors: Jean Bowler; Graham Ernest Robinson, both of Macclesfield, England

[73] Assignee: Imperial Chemical Industries Limited, London, England

[21] Appl. No.: 816,666

[22] Filed: Jul. 18, 1977

[30] Foreign Application Priority Data

Aug. 11, 1976 [GB] United Kingdom ............... 33382/76

[51] Int. Cl.$^2$ .......................................... C07C 177/00
[52] U.S. Cl. .................... 424/278; 542/426; 542/429; 260/348.55
[58] Field of Search ............... 542/426, 429; 260/348.55; 424/278

[56] References Cited

U.S. PATENT DOCUMENTS

| | | | |
|---|---|---|---|
| 3,772,350 | 11/1973 | Pike | 260/348.55 X |
| 3,899,526 | 8/1975 | Schneider | 260/348.55 X |
| 3,931,297 | 1/1976 | Crabbe | 542/426 X |
| 3,933,904 | 1/1976 | Strike | 260/348.55 X |
| 3,966,773 | 6/1976 | Bernady et al. | 260/348.55 |
| 4,028,350 | 6/1977 | Biendy | 542/426 |

*Primary Examiner*—Allen B. Curtis
*Attorney, Agent, or Firm*—Cushman, Darby & Cushman

[57] ABSTRACT

The disclosure relates to ω-aryl substituted ω-nor prostaglandin analogues bearing an oxygenated function at C-10, such as a hydroxy radical, or a 9,10- or 10,11-epoxide. A typical compound is 16-(3-chlorophenoxy)-9α,10β,11α,15α-tetrahydroxy-17,18,19,20-tetranor-5-cis,13-trans-prostadienoic acid. Also disclosed are chemical processes for the manufacture of said compounds, pharmaceutical and veterinary compositions containing said compounds, and a method of achieving luteolysis in mammals by the use of such compounds.

10 Claims, No Drawings

3,4-EPOXY-CYCLOPENTA-1,2-DIYL PROSTANES

This invention relates to novel prostane derivatives, and in particular it relates to novel prostrane derivatives which have an oxygenated substituent at C-10 of the prostane nucleus, and which possess valuable luteolytic properties. The new derivatives are therefore advantageous when used as contraceptives, for control of the oestrous cycle in mammals, for the induction of labour or for the termination of early pregnancy. The compounds may also be useful as hypotensives, for the relief of bronchospasm or as inhibitors of gastric secretion or blood platelet aggregation.

According to the invention, there is provided a prostane derivative of the formula:

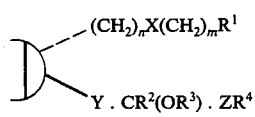

I wherein either $R^1$ is a carboxy or hydroxymethyl radical or a $C_{2-12}$ alkoxycarbonyl or alkoxymethyl radical and D is a 3,4,5-trihydroxycyclopenta-1,2-diyl radical; or $R^1$ is a carboxy or $C_{2-12}$ alkoxycarbonyl radical and D is a 3,4-epoxy-5-oxocyclopenta-1,2-diyl, 3,4-epoxy-5-hydroxycyclopenta-1,2-diyl, 3,4-dihydroxy-5-oxocyclopenta-1,2-diyl, 3,4-dihydroxycyclopent-5-en-1,2-diyl or 4-hydroxy-3-oxocyclopent-5-en-1,2-diyl radical; X is an ethylene or vinylene radical; Y is an ethylene or trans-vinylene radical; n is 1 or 2 and m is 2 to 5, provided that n and m together total 4 to 6; $R^2$ and $R^3$ which may be the same or different are each a hydrogen atom or a $C_{1-4}$ alkyl radical; Z is a direct bond, a $C_{1-3}$ alkylene radical or a $C_{1-3}$ alkyleneoxy radical, in which the oxygen is bonded to $R^4$; and $R^4$ is a phenyl or naphthyl radical optionally bearing one or more substituents selected from halogen atoms, nitro, hydroxy and phenyl radicals, and $C_{1-4}$ alkyl, alkoxy and halogenoalkyl radicals; and for those compounds wherein $R^1$ is a carboxy radical, the pharmaceutically or veterinarily acceptable salts thereof.

A suitable value for $R^1$ when it is an alkoxycarbonyl radical is, for example, a methoxycarbonyl, ethoxycarbonyl, propoxycarbonyl, butoxycarbonyl or decyloxycarbonyl radical, particularly such a radical of 2 to 5 carbon atoms, and especially a methoxycarbonyl radical.

A suitable value for $R^1$ when it is an alkoxymethyl radical is, for example, a methoxymethyl, ethoxymethyl, propoxymethyl, butoxymethyl or decyloxymethyl radical, particularly such a radical of 2 to 5 carbon atoms and especially a methoxymethyl radical.

A suitable value for $R^2$ or $R^3$, when either is an alkyl radical, is, for example, a methyl, ethyl, propyl or butyl radical, especially a methyl radical.

A suitable value for Z when it is an alkylene or alkyleneoxy radical is, for example, a methylene, ethylene, trimethylene, ethylidene, propylidene, isopropylidene, methyleneoxy, ethyleneoxy, ethylideneoxy, propylideneoxy or isopropylideneoxy radical, and particularly a methylene, ethylene, methyleneoxy or isopropylideneoxy radical.

Suitable halogen substituents in $R^4$ are, for example, chlorine, fluorine, bromine or iodine atoms, especially chlorine and fluorine atoms, and suitable $C_{1-4}$alkyl, alkoxy and halogenoalkyl radicals are, for example, methyl, ethyl, propyl, butyl, methoxy, ethoxy, propoxy, butoxy, chloromethyl and trifluoromethyl radicals, particularly methyl, methoxy and trifluoromethyl radicals. Preferred radicals $R^4$ bears only one such substituent.

A preferred value for X when it is a vinylene radical is a cis-vinylene radical.

Suitable salts are the ammonium, alkylammonium containing 1 to 4 $C_{1-6}$alkyl radicals, alkanolammonium containing 1 to 3 2-hydroxyethyl radicals, and alkali metal salts, for example the triethylammonium, ethanolammonium, diethanolammonium, sodium and potassium salts.

It is to be noted that in the compounds of the formula I, the carbon atom of the group —$CR^2(OR^3)$— is asymmetrically substituted, and that the various values for the ring D all introduce further centres of asymmetry. It is clear, therefore, that the compounds may exist in a variety of racemic and optically active forms, and it is to be understood that the useful properties of a racemate may be present to different extents in the optical isomers, and that this invention relates to any racemic and any optically active form which shows the useful properties described above, it being a matter of common general knowledge how the optically active forms may be obtained, and to determine their respective biological properties.

A preferred group of prostane derivatives of the invention comprises compounds wherein D is a 3,4,5-trihydroxycyclopenta-1,2-diyl radical, or a 3,4-epoxy-5-hydroxycyclopenta-1,2-diyl radical in which the —$Y.CR^2(OR^3).ZR^4$ side-chain is attached to C-1 and the —$CH_2X(CH_2)_3R^1$ side-chain is attached to C-2, and especially such compounds wherein D is a 3α,4β,5α-trihydroxycyclopenta-1,2-diyl or 3α,4α-epoxy-5α-hydroxycyclopenta-1,2-diyl radical, $R^1$ is a carboxy or methoxycarbonyl radical, X is a cis-vinylene radical, Y is a trans-vinylene radical, $R^2$ and $R^3$ are each a hydrogen atom, Z is a methyleneoxy radical, and $R^4$ has the meaning stated above, particularly a chlorophenyl or trifluoromethylphenyl radical, for example a 3-chlorophenyl or 3-trifluoromethylphenyl radical.

Particular preferred prostane derivatives of the invention are 16-(3-chlorophenoxy)-9α,10β,11α,15α-tetrahydroxy-17,18,19,20-tetranor-5-cis,13-trans-prostadienoic acid and 16-(3-chlorophenoxy)-9α,10α-epoxy-11α,15-dihydroxy-17,18,19,20-tetranor-5-cis,13-trans-prostadienoic acid.

The prostane derivatives of the invention may be prepared by methods known to be useful for the manufacture of chemically analogous compounds. The following processes are provided as further features of the invention, wherein $R^1,R^2, R^3, R^4,D,X,Y,$ and Z have the meanings stated above, except where specified otherwise:

(a) for those compounds wherein D is a 3,4-epoxy-5-hydroxycyclopenta-1,2-diyl radical, having the side-chain —$CH_2X(CH_2)_3R^1$ attached to C-2, $R^1$ is an alkoxycarbonyl radical and $R^2$ and $R^3$ are each a hydrogen atom, the reduction of a 15-oxo compound of the formula:

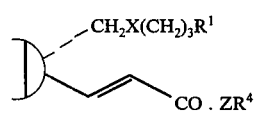

II wherein D and $R^1$ have the meanings stated immediately above, for example with aluminium tri-isopropoxide, di-isobornyloxyaluminium isopropoxide or sodium borohydride;

(b) for those compounds wherein D is a 3,4-epoxy-5-oxocyclopenta-1,2-diyl radical having the side-chain $-CH_2X(CH_2)_3R^1$ attached to C-2 and $R^1$ is an alkoxycarbonyl radical, and $R^2$ is a $C_{1-4}$alkyl radical, the oxidation of a corresponding compound wherein D is a 3,4-epoxy-5-hydroxycyclopenta-1,2-diyl radical having the side-chain $-CH_2X(CH_2)_3R^1$ attached to C-2, $R^2$ is an alkyl radical and $R^3$ has the meaning stated above, for example with chromium trioxide/pyridine complex, or with Jones' reagent (chromic acid in acetone);

(c) for those compounds wherein D is a 3,4-epoxy-5-oxocyclopenta-1,2-diyl radical having the side-chain $-CH_2X(CH_2)_3R^1$ attached to C-1, the epoxidation of a compound of the formula:

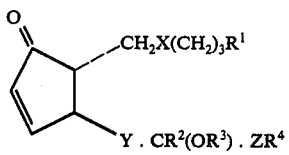   III for example with alkaline hydrogen peroxide;

(d) for those compounds wherein D is a 3,4-dihydroxy-5-oxocyclopenta-1,2-diyl or 3,4,5-trihydroxycyclopenta-1,2-diyl radical, the reaction of a corresponding compound wherein D is a 3,4-epoxy-5-oxocyclopenta-1,2-diyl or 3,4-epoxy-5-hydroxycyclopenta-1,2-diyl radical with an aqueous acid, for example aqueous sulphuric or perchloric acid;

(e) for those compounds wherein D is a 3,4-epoxy-5-hydroxycyclopenta-1,2-diyl radical, the reduction of a corresponding compound wherein D is a 3,4-epoxy-5-oxocyclopenta-1,2-diyl radical, for example with sodium borohydride;

(f) for those compounds wherein D is a 3,4,5-trihydroxycyclopenta-1,2-diyl radical, the separation of a mixture comprising said compound wherein D is a 3,4,5-trihydroxycyclopenta-1,2-diyl radical, and the corresponding compound wherein D is a 3,5-dihydroxycyclopenta-1,2-diyl radical, for example by chromatography;

(g) for those compounds wherein $R^1$ is an alkoxycarbonyl radical, the reaction either of a corresponding compound wherein $R^1$ is a carboxy radical with a $C_{1-11}$diazoalkane, or of a salt thereof with a $C_{1-11}$alkyl halide, for example an alkyl bromide or iodide;

(h) for those compounds wherein $R^1$ is a carboxy radical, the hydrolysis of a corresponding compound wherein $R^1$ is an alkoxycarbonyl radical;

(i) for those compounds wherein D is a 3,4,5-trihydroxycyclopenta-1,2-diyl radical, and $R^1$ is a hydroxymethyl radical, the reduction of a corresponding compound wherein $R^1$ is an alkoxycarbonyl radical, for example with lithium aluminium hydride;

(j) for those compounds wherein D is a 3,4,5-trihydroxycyclopenta-1,2-diyl radical, the hydrolysis of a tetrahydropyranyl derivative of the formula:

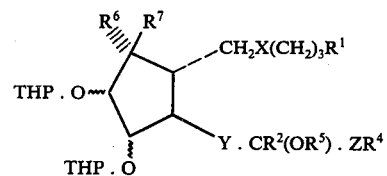   IV wherein $R^5$ is a $C_{1-4}$alkyl radical or THP, and THP is a tetrahydropyran-2-yl radical, $R^6$ is a hydroxy radical and $R^7$ is a hydrogen atom, or $R^6$ and $R^7$ together form an oxo radical, for example with an aqueous acid such as aqueous acetic acid;

(k) for those compounds wherein $R^3$ is an alkyl radical, the alkylation of a corresponding compound wherein $R^3$ is a hydrogen atom, for example with an alkyl bromide or iodide in the presence of a strong base;

(l) for those compounds wherein D is a 3,4-epoxy-5-hydroxycyclopenta-1,2-diyl, 3,4-epoxy-5-oxocyclopenta-1,2-diyl, 3,4-dihydroxycyclopent-5-en-1,2-diyl or 4-hydroxy-3-oxocyclopent-5-en-1,2-diyl radical, and $R^2$ is a hydrogen atom, the hydrolysis of a tetrahyropyran-2-yl derivative of the formula:

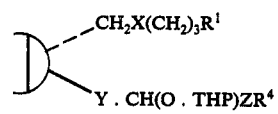   V wherein THP respresents a tetrahydropyran-2-yl radical, for example with dilute acetic acid;

(m) for those compounds wherein D is a 3,4-epoxy-5-hydroxycyclopenta-1,2-diyl or 3,4-epoxy-5-oxocyclopenta-1,2-diyl radical, $R^2$ is a $C_{1-4}$alkyl radical and n is 1, the reaction of a lactol of the formula:

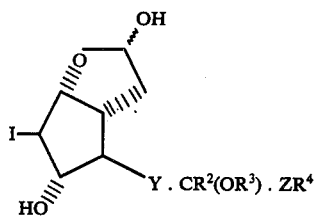   VI wherein $R^2$ is a $C_{1-4}$alkyl radical, with a (4-carboxyalkyl)triphenylphosphonium salt, for example the bromide in the presence of a base;

(n) for those compounds wherein D is a 3,4,5-trihydroxycyclopenta-1,2-diyl or 3,4-dihydroxy-5-oxocyclopenta-1,2-diyl radical, the hydroxylation, for example with osmium tetroxide, of a corresponding compound of the formula I wherein D is a 3-hydroxycyclopent-4-en-1,2-diyl or 3-oxocyclopent-4-en-1,2-diyl radical;

(o) for those compounds wherein D is a 3,4,5-trihydroxycyclopenta-1,2-diyl or 3,4-dihydroxy-5-oxocyclopenta-1,2-diyl radical, the hydrolysis with a base of a corresponding compound of the formula I wherein D is a 4-acetoxy-3-hydroxy-5-iodocyclopenta-1,2-diyl radical.

The starting material of the formula II may be obtained by reacting the acetal VII with 2,3-dihydropyran to give the tetrahydropyran-2-yl derivative VIII which is reduced with di-isobutyl aluminium hydride to the lactol IX.

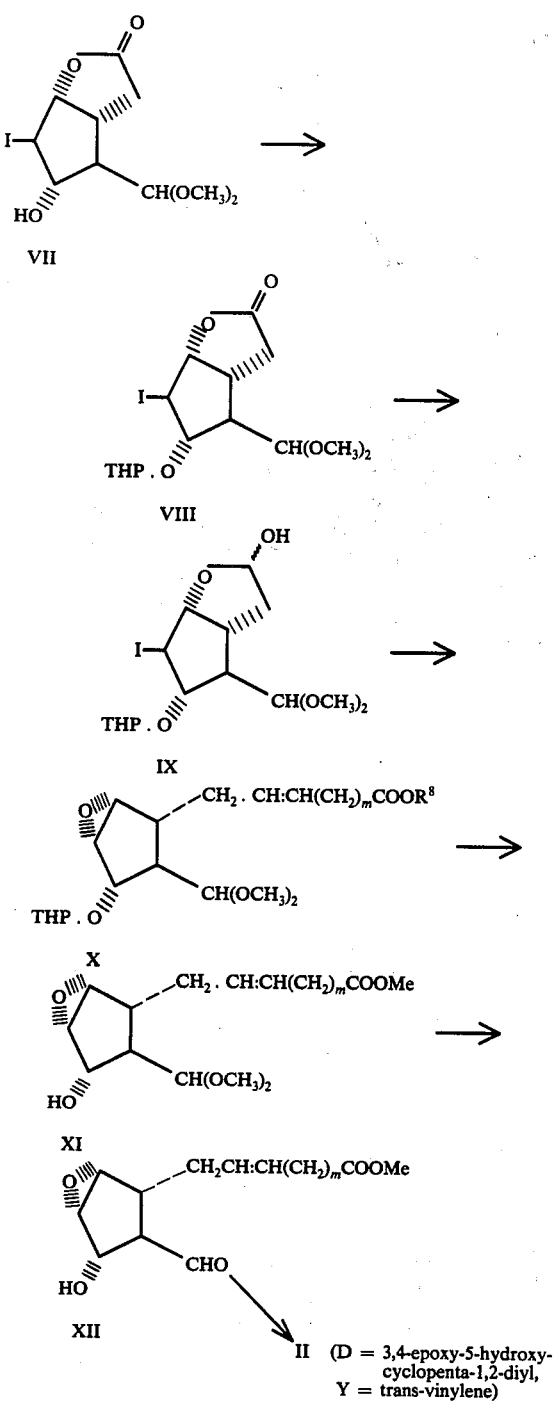

II (D = 3,4-epoxy-5-hydroxy-cyclopenta-1,2-diyl, Y = trans-vinylene)

The lactol IX is treated with a (4-carboxyalkyl)triphenylphosphonium salt to give the acid X ($R^8$ = H), which is esterified with diazomethane to the ester X ($R^8$ = $CH_3$). The tetrahydropyranyl protecting group is removed with toluene-p-sulphonic acid in methanol, giving the alcohol XI, and the acetal group is hydrolysed with toluene-p-sulphonic acid in acetone to the aldehyde XII, which is reacted with a phosphonate, $(CH_3O)_2PO.CH_2CO.ZR^4$, in the presence of a strong base to give the required starting material II.

The starting material of the formula III may be obtained by the dehydration of the corresponding compound of the formula:

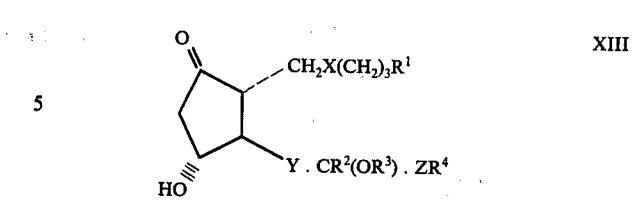

with N,N'-dicyclohexylcarbodi-imide in the presence of a cupric chloride catalyst.

The starting material of the formula IV may be obtained by treating the iodo-acetal VII with tributyl tin hydride in the presence of oxygen to give the dihydroxy-acetal XIV, which is reacted with 4-phenylbenzoyl chloride or with a tri($C_{1-4}$alkyl)silyl chloride to give the diester-acetal XV. The acetal group is hydrolysed, in a two-phase system of concentrated hydrochloric acid and chloroform optionally containing isopropanol, to give the aldehyde XVI, which is reacted with a phosphonate, $(CH_3O)_2PO.CH_2CO.ZR^4$, in the presence of a strong base to give the enone XVII. Either (a) the enone XVII is reduced, either with sodium borohydride to give an alcohol XVIII wherein Y is an ethylene radical and $R^2$ and $R^3$ are each a hydrogen atom, or with aluminium triisopropoxide or di-isobornybxyaluminium isopropoxide to give an alcohol XVIII wherein Y is a trans-vinylene radical and $R^2$ and $R^3$ are each a hydrogen atom; or (b) the enone XVII is treated with a Grignard reagent, $R^2Mg$. Halide, to give an alcohol XVIII wherein Y is a transvinylene radical, $R^2$ is an alkyl radical and $R^3$ is a hydrogen atom, which optionally may be hydrogenated to an alcohol XVIII wherein Y is an ethylene radical, $R^2$ is an alkyl radical and $R^3$ is a hydrogen atom.

Optionally, an alcohol XVIII from (a) or (b) above may be reacted with an alkyl halide in the presence of a base to give an ether XVIII wherein $R^3$ is an alkyl radical. A compound XVIII is hydrolysed to give a diol, XIX ($R^3$ = alkyl) or a triol, XIX ($R^3$ = hydrogen), which is treated with 2,3-dihydropyran to give respectively a bis(tetrahydropyran-2-yl) ($R^5$ = alkyl) or tris(-tetrahydropyran-2-yl) ($R^5$ = tetrahydropyran-2-yl) derivative XX. The lactone ring is reduced to a lactol XXI with di-isobutylaluminium hydride, and the lactol XXI is treated with an ω-(carboxyalkyl)triphenylphosphonium salt $Ph_3P^+.(CH_2)_{m+1}.COOH.X^-$ in the presence of a strong base, to give the required starting material IV.

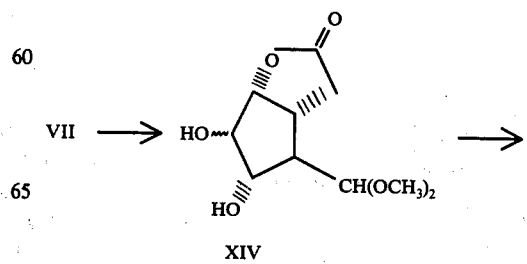

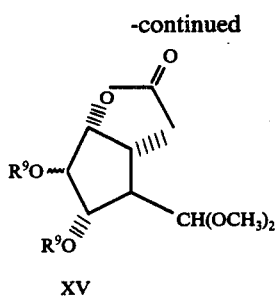

XV

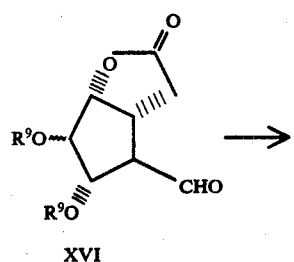

XVI

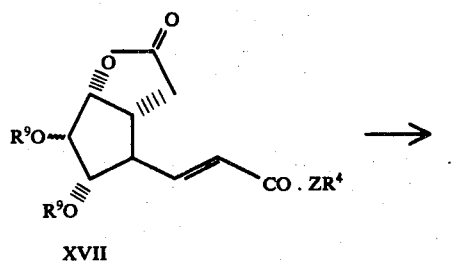

XVII

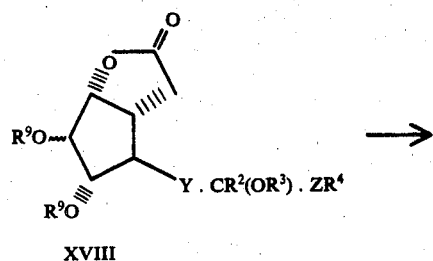

XVIII

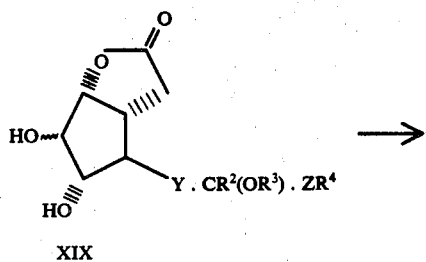

XIX

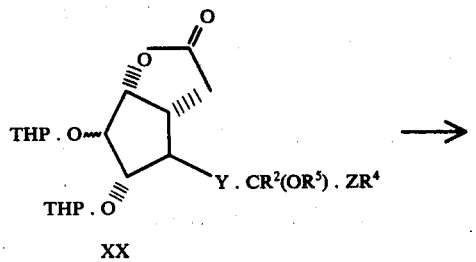

XX

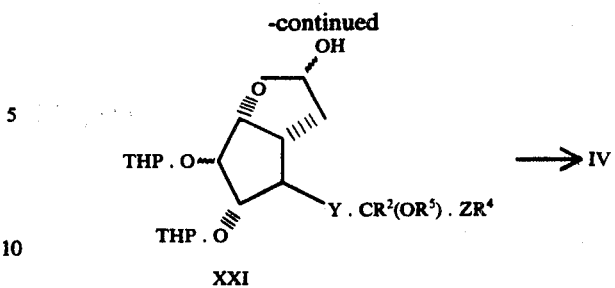

XXI $R^9$ = 4-phenylbenzoyl or tri($C_{1-4}$alkyl)silyl.

The mixture of a compound wherein D is a 3,4,5-trihydroxycyclopenta-1,2-diyl radical and the corresponding compound wherein D is a 3,5-dihydroxycyclopenta-1,2-diyl radical, which is used as the starting material in process (f), may be obtained by a modification of the multi-stage synthesis involving compounds VII, XIV to XXI, and IV described immediately above, by using a mixture of the compound XIV and the compound:

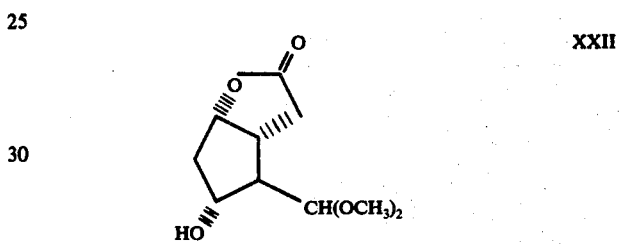

XXII (which is obtained initially from the reaction of the iodoacetal VII with tributyltin hydride, even in the absence of deliberately introduced oxygen), in place of the isolated compound XIV as described above.

The tetrahydropyran-2-yl derivative of the formula V, wherein D is a 3,4-epoxy-5-hydroxycyclopenta-1,2-diyl or 3,4-epoxy-5-oxocyclopenta-1,2-diyl radical which is used as the starting material in process (1), may be obtained by reacting the acetal VII with 4-phenylbenzoyl chloride or a tri($C_{1-4}$alkyl)silyl chloride to give a protected iodohydrin XXIII, which is hydrolysed in a two-phase system of concentrated hydrochloric acid and chloroform optionally containing isopropanol, to the aldehyde XXIV. The aldehyde XXIV is reacted with a phosphonate $(CH_3O)_2PO.CH_2COZR^4$ to give an enone XXV, and the enone XXV is either reduced, or treated with a Grignard reagent $R^2Mg$.halide as described above for the similar enone XVII, to give an alcohol XXVI, and the alcohol XXVI is protected as the tetrahydropyranyl ether XXVII. The tetrahydropyranyl ether XXVII is reduced with di-isobutylaluminium hydride to the lactol XXVIII, and the lactol XXVIII is treated with an ω-(carboxyalkyl)-triphenylphosphonium salt, $Ph_3P^+.(CH_2)_{m+1}.COOH.X^-$ to give an epoxide XXIX which is selectively hydrolysed to the required starting material, V (D = 3,4-epoxy-5-hydroxycyclopenta-1,2-diyl), which may be oxidised with Jones' reagent to the corresponding starting material wherein D is a 3,4-epoxy-5-oxocyclopenta-1,2-diyl radical.

VII →  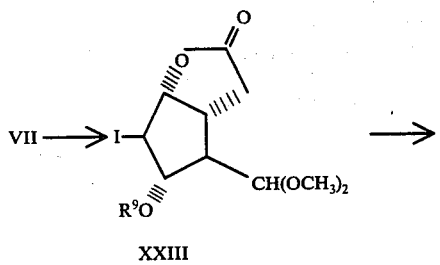 →

XXIII

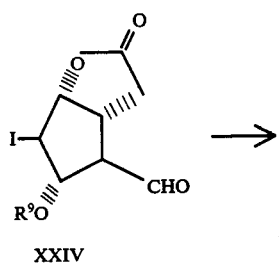 →

XXIV

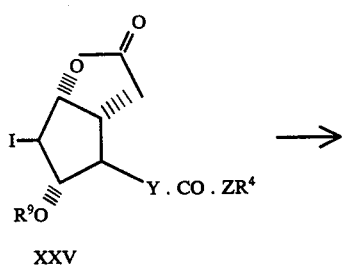 →

XXV

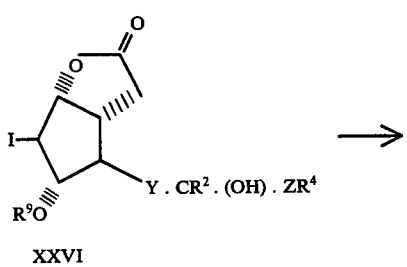 →

XXVI

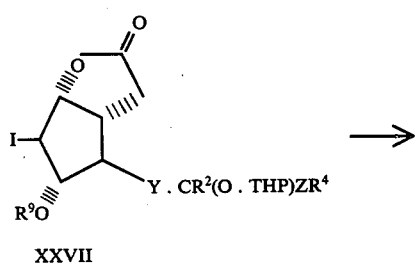 →

XXVII

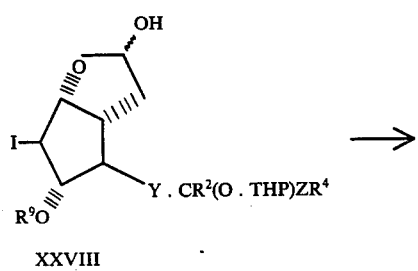 →

XXVIII

-continued

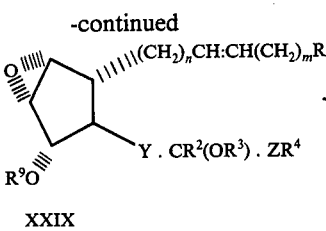 → V

XXIX

The starting material of the formula V wherein D is a 3,4-dihydroxycyclopent-5-en-1,2-diyl radical may be prepared by hydrolysing the acetal 4β-dimethoxymethyl-5α,6α-epoxy-2,3,3aβ,6aβ-tetrahydro-2-oxocyclopenteno[b]furan to the unsaturated aldehyde 4β-formyl-2,3,3aβ,6aβ-tetrahydro-6α-hydroxy-2-oxocyclopentadieno[1,2-b]furan, which is used in place of the aldehyde XXIV in the reaction sequence described above, omitting the final hydrolysis of XXIX. The starting material so obtained may be oxidised with Jones' reagent to the corresponding starting material wherein D is a 4-hydroxy-3-oxocyclopent-5-en-1,2-diyl radical.

The lactol of the formula VI wherein n is 1, which is used as the starting material in process (m), may be obtained by hydrolysing the acetal VIII to give the aldehyde XXX, which is reacted with a phosphonate $(CH_3O)_2PO.CH_2CO.ZR^4$ to give an enone XXXI. The enone XXXI is either reduced or treated with a Grignard reagent, $R^2Mg$.halide, as described above for the similar enone XVII, to give an alcohol XXXII, which may optionally be alkylated as described above for the similar alcohol XVIII, and the alcohol XXXII is reduced to the lactol XXXIII, which is hydrolysed to remove the tetrahydropyranyl group, and give the required starting material VI.

VIII → 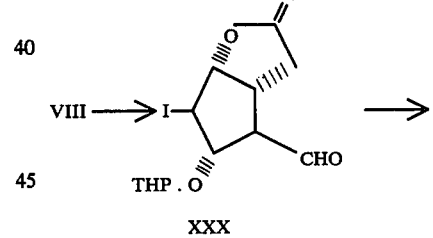 →

XXX

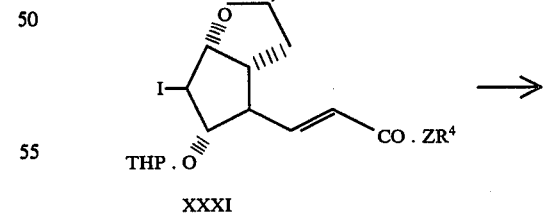 →

XXXI

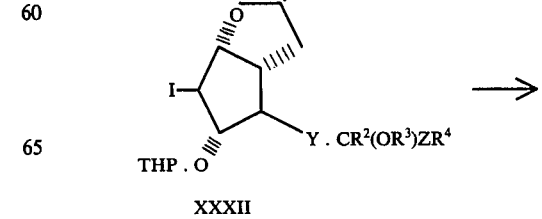 →

XXXII

-continued

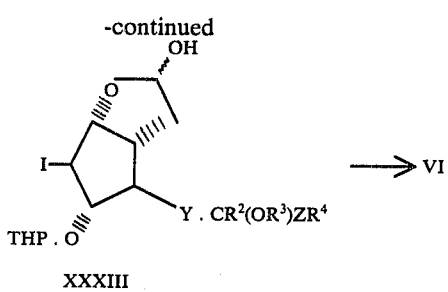

XXXIII

It is, of course, to be understood that an optically active compound of the invention may be obtained either by resolving a corresponding racemate, or by carrying out the above described reaction sequences starting from an optically active intermediate, As stated above, the compounds of the invention possess luteolytic properties, and in particular they are more active as luteolytic agents and less active as smooth muscle stimulants than the naturally occurring prostaglandins. Thus, for example methyl 16-(3-chlorophenoxy)-9α,10α-epoxy-11α,15-dihydroxy-17,18,19,20-tetranor-5-cis,13-transprostadienoate acid is approximately 100 times as active as natural prostaglandin $F_2\alpha$ as a luteolytic agent in hamsters (subcutaneous dosing). No indications of toxicity have been noted, at the optimum luteolytic doses, in experimental animals.

When a compound of the invention is to be used for the induction of labour, it is used in the same way as it is known to use the naturally occurring prostaglandin $E_2$, that is by administering a sterile, substantially aqueous solution containing from 0.01 to 10μg./ml., preferably 0.01 to 1μg./ml. of the compound, by intravenous infusion, or by transcervical extra-amniotic or intraamniotic infusion until labour commences.

Also, for this purpose, the compounds of the invention may be used in combination, or concurrently, with a uterine stimulant, for example oxytocin, in the same way that it is known to use prostaglandin $F_2\alpha$ in combination, or concurrently, with oxytocin for the induction of labour.

When a compound of the invention is to be used for the control of the oestrus cycle in animals, it may be used in the same way as it is known to use the luteolytic prostaglandin analogues cloprostenol and fluprostenol. It may also be used in combination, or concurrently, with a gonadotrophin, for example PMSG (pregnant mare serum gonadotrophin) or HCG (human chorionic ganodotrophin) to hasten the onset of the next cycle.

Thus, according to a further feature of the invention there is provided a pharmaceutical or veterinary composition comprising a prostane derivative of the invention, together with a pharmaceutically or veterinarily acceptable diluent or carrier.

The compositions may be in a form suitable for oral administration, for example tablets or capsules, in a form suitable for inhalation, for example an aerosol or a solution suitable for spraying, in a form suitable for parenteral administration, for example sterile injectable aqueous or oily solutions or suspensions, or in the form of a suppository or pessary, suitable for anal or vaginal use. As stated above, when the compound of the invention is to be used for the induction of labour in childbirth, a preferred composition of the invention is a sterile, substantially aqueous solution containing from 10 to 250μg/ml., preferably 50 to 100μg./ml. of the prostane derivative.

The compositions of the invention may be prepared by conventional means, and may incorporate conventional excipients.

The invention is illustrated, but not limited, by the following Examples. $R_F$ values refer to thin layer chromatography on silica gel plates supplied commercially by Merck of Darmstadt, and the spots were detected either by fluorescence, or by spraying the plates with a solution of ceric ammonium nitrate in sulphuric acid.

EXAMPLE 1

Mother liquors from the crystallisation of racemic sodium 16-(3-chlorophenoxy)-9α,11α,15α-trihydroxy-17,18,19,20-tetranor-5-cis, 13-trans-prostadienoate (cloprostenol, "Estrumate" -trade mark) were acidified and evaporated to dryness. The residue (20 g.) was dissolved in chloroform (60 ml.) and applied to a silica gel chromatography column (1 kg.) made up in chloroform. The column was eluted with a mixture of hexane/ethanol/acetic acid (90:10:0.1 by volume), and 45 fractions (200 ml. each) were collected and discarded. The eluting solvent was increased in polarity so that it contained 20% by volume of ethanol, and a further 40 × 200 ml. fractions were collected, and discarded. The eluting solvent was again increased in polarity so that it contained 25% by volume of ethanol. Four 200 ml. fractions were discarded, but the following seven 200 ml. fractions were combined, and evaporated to dryness. A portion (50 mg.) of the residue was dissolved in a mixture of methanol and ethyl acetate, and applied to a silica gel preparative thin-layer chromatography plate, which was developed with 7.5% v/v acetic acid in ethyl acetate. The developed plate was examined in ultraviolet light, and the band having $R_F=0.18$ was scraped off the plate. The scrapings were extracted with methanol (3 × 25 ml.), and the methanol solution was evaporated to dryness. The residue was treated with ethyl acetate (10 ml.) and saturated brine (2 ml.), the ethyl acetate later was separated and dried, and the solvent was evaporated under reduced pressure to give racemic 16-(3-chlorophenoxy)-9α,10β,11α,15α-tetrahydroxy-17,18,19,20-tetranor-5-cis, 13-transprostadienoic acid.

The cloprestenol, which was crystallised to provide the mother liquors used as the starting material for the above process, was prepared from 4β-dimethoxymethyl-2,3,3aβ,6aβ-tetrahydro-5α-hydroxy-6β-iodo-2-oxocyclopenteno[b]furan by the process described in United Kingdom Patent Application No. 53,757/74, and in corresponding applications in other countries, to give 4 β-[4-(3-chlorophenoxy)-3-oxobut-1-transenyl]-2,3,3aβ,6aβ-tetrahydro-5α-hydroxy-2-oxocyclopenteno[b]-furan, which was converted to 4β-[4-(3-chlorophenoxy)-3α-hydroxybut-1-trans-enyl]-2,3,3aβ,6aβ-tetrahydro-5α-hydroxy-2-oxocyclopenteno[b]furan, by the process described in United Kingdom Patent Application No. 25012/75, and in corresponding applications in other countries, which in turn was converted to cloprostenol by the process described in United Kingdom Patent No. 1,350,971, and in corresponding applications in other countries.

EXAMPLE 2

To a solution of methyl 16-(3-chlorophenoxy)-9α,10α-epoxy-11α-hydroxy-15-oxo-17,18,19,20-tetranor-5-cis, 13-transprostadienoate (8 mg.) in toluene (0.5 ml.) was added a solution of di-isobornyloxyaluminium isopropoxide (100 μl. of a 0.36 M solution in toluene).

After 2 hours at room temperature saturated sodium hydrogen tartrate solution was added, followed by ethyl acetate (10 ml.). The organic phase was separated and dried, and the solvents were evaporated. The crude product was chromatographed on silica gel, using acetone as eluant to yield methyl 16-(3-chlorophenoxy)-9α,10α-epoxy-11α,15-dihydroxy-17,18,19,20-tetranor-5-cis, 13-trans-prostadienoate, as a mixture of epimers, $R_F = 0.4$ and $0.45$/ethyl acetate). The n.m.r. spectrum in deuterated acetone showed the following characteristic bands (δ values):
6.9 - 7.4, broad multiplet, 4 aromatic protons
5.3 - 5.7, broad multiplet, 4 olefinic protons
3.55, singlet, 3H, —COOMe
3.35, multiplet, 2H, C-9 and C-10 protons
The mass spectrum of the bis (trimethylsilyl) derivative showed

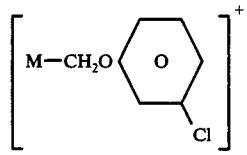

= 439.2303, calculated for $C_{22}H_{39}O_5Si_2 = 439.2335$.

The enone used as starting material in the above process may be obtained as follows:

To a solution of 4β-dimethoxymethyl 2,3,3aβ-6aβ-tetrahydro-5α-hydroxy-6β-iodo-2-oxocyclopenteno[b]furan (1.026 g.) in toluene (10 ml.), under an atmosphere of nitrogen, were added successively redistilled 2,3-dihydropyran (4.2 ml.) and a solution of anhydrous toluene-p-sulphonic acid in tetrahydrofuran(1 ml. of a 1% w/v solution). After 15 minutes, pyridine (0.5 ml.) was added, followed by ethyl acetate (100 ml.). The solution was washed successively with saturated sodium bicarbonate and brine, and was dried, and the solvents were evaporated to give the tetrahydropyranyl ether, 4β-dimethoxymethyl-2,3,3aβ,6aβ-tetrahydro-6-β-iodo-5α-(tetrahydropyran-2-yloxy)-2oxocyclopenteno[b]furan, as a clear oil, $R_F = 0.8$ (10% v/v acetone in chloroform).

To a solution of the tetrahydropyranyl ether (1.3 g.) in dry toluene (25 ml.), under an atmosphere of nitrogen at −78° C., was added di-isobutyl aluminium hydride (3 ml. of a 1.2 M solution in toluene). After 15 minutes, the reaction was quenched with methanol (5 ml.), and after a further 15 minutes at room temperature, a mixture of 1:1 v/v saturated brine and water (25 ml.) was added, and the mixture was extracted with ethyl acetate (3 × 50 ml.). The extract was dried, and the solvents were evaporated to give the lactol, 4β-dimethoxymethyl-2,3,3aβ,6aβ-tetrahydro-2-hydroxy-6β-iodo-5α-(tetrahydropyran-2-yloxy)cyclopenteno[b]furan, $R_F = 0.4$ (10% v/v acetone in chloroform).

A stirred solution of (4-carboxybutyl)triphenylphosphonium bromide (8.86 g.) in dry toluene (120 ml.) was treated under argon at 90° C. with potassium t-butoxide (4.02 g.) to form a solution of the corresponding ylide.

The ylide solution (70 ml.) was then added to a solution of the lactol (1.5 g.) in dry toluene (30 ml.) at room temperature, and the mixture was stirred for 30 minutes, and then extracted with water (3 × 10 ml.). The aqueous extracts were combined, acidified to pH 4.5 with saturated oxalic acid, and extracted with ether (4 × 10 ml.). The extracts were then washed with brine, dried over magnesium sulphate and filtered, and the solvent was evaporated to give the acid, 7-[2β-dimethoxymethyl-4α,5α-epoxy-3α-(tetrahydropyran-2-yloxy)cyclopent-1α-yl]hept-5-cis-enoic acid, $R_F = 0.4$ (ethyl acetate).

To a solution of the acid (770 mg.) in diethyl ether (10 ml.) at 0° C. was added an excess of a solution of diazomethane in diethyl ether. After 10 minutes the solvents were evaporated to give the ester, methyl 7-[2β-dimethoxymethyl-4α,5α-epoxy-3α-(tetrahydropyran-2-yloxy)cyclopent-1α-yl]hept-5-cis-enoate, $R_F = 0.6$ (50% v/v ethyl acetate in toluene. The mass spectrum showed: $(M—CH_3OH)^+ = 366.2025$ (calculated for $C_{20}H_{30}O_6 = 366.2042$).

To a solution of the ester (235 mg.) in dry methanol (10 ml.) was added a solution of anhydrous toluene-p-sulphonic acid in tetrahydrofuran (500 μl. of a 1% w/v solution). After 25 minutes, pyridine (0.1 ml.) was added, followed by ethyl acetate (50 ml.). The solution was washed successively with saturated sodium bicarbonate solution and brine, and was dried. Evaporation of the solvents gave the hydroxy-acetal, methyl 7-[2β-dimethoxymethyl-4α,5α-epoxy-3α-hydroxycyclopent-1α-yl]hept-5-cis-enoate, $R_F = 0.4$ (ethyl acetate).

To a solution of the hydroxy-acetal (50 mg.) in a mixture of acetone (3 ml.) and water (1 ml.) was added toluene-p-sulphonic acid (10 mg.). The mixture was heated under reflux for 30 minutes, neutralised with sodium bicarbonate and diluted with ethyl acetate (30 ml.). The mixture was washed with brine, the organic phase was separated and dried, and the solvents were evaporated to give the aldehyde, methyl 7-[4α,5α-epoxy-2β-formyl-3α-hydroxycyclopent-1α-yl]hept-5-cis-enoate, $R_F = 0.5$ (ethyl acetate). The n.m.r. spectrum in deuterated acetone showed the following characteristic bands (δ values):
9.8, doublet, 1H, —CHO
5.4 -5.6, multiplet, 2 olefinic protons
3.6, singlet, 3H, —COOCH₃

A solution of dimethyl [3-(3-chlorophenoxy-2-oxopropyl]phosphonate (44mg.) in dry 1,2-dimethoxyethane (2ml.) at −78° C. was treated with n-butyllithium (106ml. of a 1.23M solution in pentane), and the mixture was stirred for 15 minutes. To this mixture was added a solution of the aldehyde (35 mg.) in 1,2-dimethoxyethane (1 ml.), after 18 hours, the reaction mixture was neutralised with glacial acetic acid and all of the solvents were evaporated, to give the required enone starting material, methyl 16-(3-chlorophenoxy)-9α,10α-epoxy-11α-hydroxy-15-oxo-17,18,19,20-tetranor-5-cis, 13-trans-prostadienoate, $R_F = 0.8$ (ethyl acetate). The n.m.r. spectrum in deuterated acetone showed the following characteristics bands (δ values):
6.8 - 7.3, broad multiplet, 4 aromatic + 1 olefinic protons.
6.4, doublet, 1H, C-14 proton
5.55, multiplet, 2 olefinic protons
3.4, multiplet, 2H, C-9 and C-10 protons.

EXAMPLE 3

|  | % w/v |
| --- | --- |
| Methyl 16-(3-chlorophenoxy)-9α,10α-epoxy-11α,15-dihydroxy-17,18,19,20-tetranor-5-cis, 13-trans-prostadienoate | 0.003 |
| Sodium phosphate B.P. | 2.90 |
| Sodium acid phosphate B.P. | 0.30 |

| | % w/v |
|---|---|
| Water for injection | to 100 |

The sodium phosphate B.P. was dissolved in about 80% of the water, followed by the prostane derivative and, when that had dissolved, the sodium acid phosphate B.P. The solution was made up to volume with water for injection and the pH was checked to be between 6.7 and 7.7. The solution was filtered to remove particulate matter, sterilised by filtration, and filled into pre-sterilised neutral glass ampoules under aseptic conditions. Immediately before use, the contents of an ampoule are diluted in sodium chloride B.P. for administration.

The prostane derivative may, of course, be replaced by an equivalent amount of another prostane derivative of the invention, to give other sterile aqueous solutions.

EXAMPLE 4

To a solution of 16-(3-chlorophenoxy)-15-hydroxy-9-oxo-17,18,19,20-tetranor-5-cis,10,13-trans-prostatrienoic acid (20mg.) in methanol (0.5ml.) were added successively, at −20° C., hydrogen peroxide (100 volume, 35μl.) and 1N sodium hydroxide (75μl.). After one-half hour, the mixture was neutralised with sodium hydrogen tartrate and the methanol was evaporated. The residue was extracted with ethyl acetate (3 × 10ml.), the extracts were washed with brine and the solvent was evaporated. The residue was purified by thin layer chromatography on silica gel, using 10% v/v methanol in methylene chloride as the developing solvent, to give 16-(3-chlorophenoxy)-10α,11α-epoxy-15-hydroxy-9-oxo-17,18,19,20-tetranor-5-cis,13-trans-prostadienoic acid, $R_F = 0.5$. The n.m.r. spectrum in deuterated acetone showed the following characteristic bands (δ values):

6.9–7.4, broad multiplet, 4H, aromatic protons.
5.3–5.9, broad multiplet, 4H, olefinic protons.
3.2–4.7, broad multiplet, 3H, >C$\underline{H}$—O— — +exchangeable protons.

The mass spectrum of the 9-methoxime tris(trimethylsilyl)derivative (in which the epoxide has been opened to

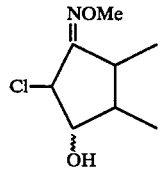

with methoxyamine hydrochloride) showed $M^+ = 701$, (calculated for $C_{32}H_{53}O_6NCl_2Si_3 = 701$).

The 16-(3-chlorophenoxy)-15-hydroxy-9-oxo-17,18,19,20-tetranor-5-cis,10,13-trans-prostatrienoic acid used as starting material in the above process may be obtained by heating a solution of 16-(3-chlorophenoxy)-11α,15-dihydroxy-9-oxo-17,18,19,20-tetranor-5-cis,13-trans-prostadienoic acid (200mg.) in a 2:1 v/v mixture of acetic acid and water (5ml.) to 60° C., stirring for 18 hours, then evaporating all solvents and purifying the residue by thin layer chromatography on silica gel, eluting with ethyl acetate, $R_F = 0.2$. The n.m.r. spectrum in deuterioacetone showed the following characteristic bands (δ values):

6.9–7.8, multiplets, 4 aromatic + 1 olefinic proton 5.5–6.3, multiplets, 5 olefinic protons
3.5–4.5, broad multiplets, 3 × >C$\underline{H}$—O— + 2 exchangeable protons.

EXAMPLE 5

To a solution of 16-(3-chlorophenoxy)-10α,11α-epoxy-15-hydroxy-9-oxo-17,18,19,20-tetranor-5-cis,13-trans-prostadienoic acid (21mg.) in methanol (0.5ml.) at 0° C. was added sodium borohydride (5mg.). The mixture was stirred for 1½ hours and neutralised with aqueous oxalic acid, and the solvent was evaporated. The residue was adjusted to pH 4 with aqueous oxalic acid and extracted with ethyl acetate (3 × 10ml.). The combined extracts were washed with saturated brine and dried, and the solvent was evaporated. The residue was purified by thin layer chromatography on silica gel, using 1% v/v acetic acid in ethyl acetate as the developing solvent, to give 16-(3-chlorophenoxy)-10α,11α-epoxy-9α,15-dihydroxy-17,18,19,20-tetranor-5-cis,13-trans-prostadienoic acid, $R_F = 0.50$, and 16-(3-chlorophenoxy)-10α,11α-epoxy-9β,15-dihydroxy-17,18,19,20-tetranor-5-cis,13-trans-prostadienoic acid, $R_F = 0.50$ and 0.55. The n.m.r. spectrum of each product in deuterated acetone showed the following characteristic bands (δ values):

6.9–7.4, broad multiplet, 4H, aromatic protons.
5.2–5.9, broad multiplet, 4H, olefinic protons + 3 exchangeable protons.

The mass spectrum of the tris(trimethylsilyl) derivative of each product showed $M^+ = 638$ (calculated for $C_{31}H_{51}O_6ClSi_3 = 638$).

EXAMPLE 6

A solution of 16-(3-chlorophenoxy)-9α-hydroxy-10,15-bis(tetrahydropyran-2-yloxy)-17,18,19,20-tetranor-5-cis,11,13-trans-prostatrienoic acid (21mg.) in 1.5ml. of a 2:1 v/v mixture of acetic acid and water was stirred at 40° C. for 3 hours. The solvents were evaporated and the residue was chromatographed on silica gel plates, using 10% v/v methanol in ethyl acetate as the developing solvent, to give 16-(3-chlorophenoxy)-9α,10,15-trihydroxy-17,18,19,20-tetranor-5-cis,11, 13-trans-prostatrienoic acid, as a mixture of isomers, $R_F = 0.3$ and 0.35. The n.m.r. spectrum in deuterated acetone showed the following characteristic bands (δ values):

6.9–7.4, broad multiplet, 4 aromatic protons
5.5–6.5, broad multiplet, 5 olefinic protons The mass spectrum of the tetra(trimethylsilyl) derivative showed $M^+ = 710$ (calculated for $C_{34}H_{59}O_6ClSi_4 = 710$).

The bis(tetrahydropyranyl ether) used as starting material in the above process may be obtained as follows:

4β-Dimethoxymethyl-2,3,3aβ,6aβ-tetrahydro-5α-hydroxy-6β-iodo-2-oxocyclopenteno[b]furan (34.2g.) was dissolved in dimethylsulphoxide (300ml., dried over 4A molecular sieve), sodium borohydride (5.7g.) was added, and the mixture was stirred at room temperature for 23 hours. Water (10ml.) was added cautiously, followed by acetic acid (10ml.) to bring the solution to pH 5, and more water (250ml.), and the solution was then extracted with methylene dichloride (2 × 250ml.). The combined extracts were washed with water (5 × 250ml.) and dried, the solvent was evaporated, and the residue was crystallised from methanol to give the epoxy-acetal, 4α-dimethoxymethyl-5α,6α-epoxy-2,3,3aβ,6aβ-tetrahydro-2-oxocyclopenteno[b]furan, m.p. 97°–99° C.

To a solution of the epoxy-acetal (50mg.) in acetone (3ml.) and water (1ml.) was added toluene-p-sulphonic acid (10mg.). The mixture was refluxed for 18 hours, neutralised, and diluted with ethyl acetate (20ml.). The mixture was washed with brine, and the organic phase was separated, dried and evaporated to dryness, to give the aldehyde, 4β-formyl-2,3,3aβ,6aβ-tetrahydro-6-hydroxy-2-oxocyclopentadieno[1,2-b]furan, $R_F$ = 0.5 (ethyl acetate). The n.m.r. spectrum in deuterated acetone showed the following characteristic bands (δ values):

9.77, singlet, 1H, formyl proton.
6.93, multiplet, 1H, olefinic proton.
5.05, multiplet, 2H, >C$\underline{H}$—O— protons.

A solution of [3-(3-chlorophenoxy)-2-oxopropyl]-phosphonate (44mg.) in dry 1,2-dimethoxyethane (2ml.) at −78° C. was treated with n-butyl-lithium (106μl. of a 1.23M solution in pentane), the mixture was stirred for 15 minutes, and a solution of the aldehyde (30mg.) in 1,2-dimethoxyethane (1ml.) was added. After 4 hours the reaction mixture was neutralised with glacial acetic acid, and all the solvents were evaporated to give the required enone, 4β-[4-(3-chlorophenoxy)-3-oxobut-1-trans-enyl]-2,3,3aβ,6aβ-tetrahydro-6-hydroxy-2-oxocyclopentadieno[1,2-b]furan, $R_F$ = 0.5 (ethyl acetate). The n.m.r. spectrum in deuterated acetone showed the following characteristic bands (δ values):

6.3–7.5, broad multiplet, 4 aromatic protons + 3 olefinic protons.
4.9–5.1, multiplet, >C$\underline{H}$—O—, 4 protons.

To a solution of the enone (85mg.) in toluene (2ml) was added a solution of di-isobornyloxyaluminium isopropoxide (1.4ml. of a 36M solution). After 3 hours at room temperature saturated sodium hydrogen tartrate solution was added, followed by ethyl acetate (30ml.), the organic phase was separated and dried, and the solvents were evaporated. The crude product was chromatographed on silica gel, using acetone as eluant, to yield the diol, 4β-[4-(3-chlorophenoxy)-3-hydroxybut-1-transenyl]- -2,3,3aβ, 6aβ-tetrahydro-6-hydroxy-2-oxocyclopentadieno[1,2-b]furan as a mixture of epimers, $R_F$ = 0.5 and 0.6 (ethyl acetate).

To a solution of the epimeric diols (54mg.) in methylene dichloride (1ml.), under an atmosphere of nitrogen, were added successively redistilled dihydropyran (0.2ml.) and a solution of toluene-p-sulphonic acid in tetrahydrofuran (20μl. of a 1%w/v solution). After 10 minutes, pyridine (2 drops) was added, followed by ethyl acetate (20ml.). The solution was washed successively with saturated sodium bicarbonate solution and saturated brine, and was then dried. Evaporation of the solvents gave a mixture of epimeric bis(tetrahydropyranyl ethers) 4β-[4-(3-chlorophenoxy)-3-(tetrahydropyran-2-yloxy)but-1-transenyl]-2,3,3aβ,6aβ-tetrahydro-2-oxo-6-(tetrahydropyran-2-yloxy)cyclopentadieno[1,2-b]furan, as a clear oil, $R_F$ = 0.7 (50% v/v ethyl acetate in toluene).

To a solution of the epimeric bis(tetrahydropyranyl ether) (60mg.) in dry toluene (3ml.) under an atmosphere of dry nitrogen at −78° C. was added 0.4ml. of a 1.22M solution of di-isobutylaluminium hydride in toluene. After 15 minutes, the reaction was quenched by the addition of methanol (1ml.), and after a further 15 minutes at room temperature, a mixture of 1:1 v/v saturated brine/water (3ml.) was added. The mixture was extracted with ethyl acetate (3 × 20ml.), the extracts were washed with saturated brine and dried, and the solvents were evaporated to give the lactol, 4β-[4-(3-chlorophenoxy)-3-(tetrahydropyran-2-yloxy)but-1-trans-enyl]-2,3,3aβ,6aβ-tetrahydro-2-hydroxy-6-(tetrahydropyran-2-yloxy)cyclopentadieno[1,2-b]furan, $R_F$ = 0.6 (50% v/v ethyl acetate in toluene).

A stirred solution of (4-carboxybutyl)triphenyl phosphonium bromide (886mg.) in dry toluene (12ml.) was treated under an atmosphere of argon at 90° C. with potassium t-butoxide (402mg.) to form a solution of the corresponding ylide. The ylide solution (3ml.) was then added to a solution of the lactol (55mg.) in dry toluene (1ml.) at room temperature, the mixture was stirred for 1 hour and was then extracted with water (3 × 2ml.). The aqueous extracts were combined, acidified to pH 4 with saturated oxalic acid, and extracted with diethyl ether (4 × 5ml.). The combined ether extracts were washed with brine and dried, and the solvent was evaporated to give the required starting material, 16-(3-chlorophenoxy)-9α-hydroxy-10,15-bis(tetrahydropyran-2-yloxy)-17,18,19,20-tetranor-5-cis,11,13-trans-prostatrienoic acid, $R_F$ = 0.5 (ethyl acetate).

What we claim is:
1. A prostane derivative of the formula:

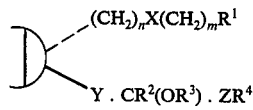

wherein $R^1$ is carboxy or $C_{2-12}$ alkoxycarbonyl and D is 3,4-epoxy-5-oxocyclopenta-1,2-diyl or 3,4-epoxy-5-hydroxycyclopenta-1,2-diyl, X is ethylene or vinylene; Y is ethylene or trans-vinylene; n is 1 or 2 and m is 2 to 5, provided that n and m together total 4 to 6; $R^2$ and $R^3$ which may be the same or different are each hydrogen or $C_{1-4}$ alkyl; Z is a direct bond, $C_{1-3}$ alkylene or $C_{1-3}$ alkyleneoxy, in which the oxygen is bonded to $R^4$; and $R^4$ is phenyl or naphthyl optionally bearing one or more substituents selected from halogen, nitro, hydroxy and phenyl, and $C_{1-4}$ alkyl, alkoxy and halogenoalkyl; and for those compounds wherein $R^1$ is carboxy, the pharmaceutically or veterinarily acceptable salts thereof.

2. The prostane derivative of claim 1 wherein $R^1$ is carboxy or $C_{2-12}$ alkoxycarbonyl selected from the group consisting of methoxycarbonyl, ethoxycarbonyl, propoxycarbonyl, butoxycarbonyl and decyloxycarbonyl, $R^2$ and $R^3$ are each hydrogen or methyl, ethyl, propyl or butyl, X is cis-vinylene, Z is a direct bond or methylene, ethylene, trimethylene, ethylidene, propylidene, isopropylidene, methyleneoxy, ethyleneoxy, ethylideneoxy, propylideneoxy or isopropylideneoxy, and $R^4$ is phenyl or naphthyl optionally bearing a chlorine, fluorine, bromine, iodine, methyl, ethyl, propyl, butyl, methoxy, ethoxy, propoxy, butoxy, chloromethyl or trifluoromethyl substituent, and the ammonium, alkylammonium containing 1 to 4 $C_{1-6}$ alkyl radicals, alkanolammonium containing 1 to 3 2-hydroxyethyl radicals, and alkali metal salts thereof.

3. The prostane derivative of claim 1 wherein D is 3,4-epoxy-5-hydroxycyclopenta-1,2-diyl in which the -Y.CR²(OR₃).ZR⁴ side-chain is attached to C-1 and the —CH₂X(CH₂)₃R¹ side-chain is attached to C-2.

4. The prostane derivative of claim 1 wherein D is 3α,4α-epoxy-5α-hydroxycyclopenta-1,2-diyl, $R^1$ is carboxy or methoxycarbonyl, X is cis-vinylene, Y is trans-vinylene, $R^2$ and $R^3$ are each hydrogen, Z is methyleneoxy, and $R^4$ has the meaning stated in claim 1.

5. The prostane derivative of claim 4 wherein $R^4$ is a chlorophenyl or trifluorometylphenyl radical.

6. The prostane derivative of claim 5 wherein $R^4$ is a 3-chlorophenyl or 3-trifluoromethylphenyl radical.

7. 16-(3-Chlorophenoxy)-9α,10β,11α,15α-tetrahydroxy-17,18,19,20-tetranor-5-cis,13-trans-prostadienoic acid.

8. 16-(3-Chlorophenoxy)-9α,10α-epoxy-11α,15-dihydroxy-17,18,19,20-tetranor-5-cis,13-trans-prostadienoic acid.

9. A pharmaceutical or veterinary luteolytic composition which comprises an effective amount of the prostane derivative of claim 1 and a pharmaceutically or veterinarily acceptable diluent or carrier.

10. A method of inducing luteolysis in a mammalian host requiring such treatment which comprises administering to said host a luteolytically effective amount of the prostane derivative of claim 1.

* * * * *